United States Patent
Ferguson (10) Patent No.: US 6,972,006 B2
(45) Date of Patent: Dec. 6, 2005

(54) SYRINGE DEVICE WITH RESISTIVE RIDGES AND METHODS OF USE

(75) Inventor: Gary William Ferguson, Burnaby (CA)

(73) Assignee: G6 Science Corp., Burnaby (CA)

( * ) Notice: Subject to any disclaimer, the term of this patent is extended or adjusted under 35 U.S.C. 154(b) by 262 days.

(21) Appl. No.: 10/246,600

(22) Filed: Sep. 18, 2002

(65) Prior Publication Data

US 2004/0054332 A1    Mar. 18, 2004

(51) Int. Cl.$^7$ .............................................. A61M 5/00
(52) U.S. Cl. ...................................... 604/208; 604/186
(58) Field of Search ......................... 604/82, 218, 220, 604/221, 230, 186, 191, 208, 209, 210

(56) References Cited

U.S. PATENT DOCUMENTS

| | | | |
|---|---|---|---|
| 2,549,417 A | | 4/1951 | Brown |
| 2,591,046 A | | 4/1952 | Brown |
| 2,720,880 A | | 10/1955 | Whitaker et al. |
| 3,934,586 A | | 1/1976 | Easton et al. |
| 4,137,917 A | | 2/1979 | Cohen |
| 4,430,079 A | | 2/1984 | Thill |
| 4,469,482 A | | 9/1984 | Lissenburg |
| 4,976,704 A | | 12/1990 | McLees |
| 4,995,869 A | * | 2/1991 | McCarthy .................... 604/110 |
| 5,000,735 A | | 3/1991 | Whelan |
| 5,045,063 A | * | 9/1991 | Spielberg .................... 604/110 |
| 5,259,732 A | | 11/1993 | Stern |
| 5,295,966 A | | 3/1994 | Stern |
| 5,389,070 A | | 2/1995 | Morell |
| 5,480,064 A | | 1/1996 | Yan |

(Continued)

FOREIGN PATENT DOCUMENTS

DE    1 557 037    3/1970

(Continued)

OTHER PUBLICATIONS

International Search Report dated Jan. 22, 2004.

*Primary Examiner*—Sharon Kennedy
(74) *Attorney, Agent, or Firm*—Trexler, Bushnell, Giangiorgi, Blackstone & Marr, Ltd (57) ABSTRACT

A syringe device incorporating ridges that cause resistive changes to the movement of the syringe gasket or plunger, thereby providing user feedback as to the position and speed of plunger movement. Such user feedback may be useful in stressful situations, under poor lighting conditions or in other unfavorable circumstances. Additionally, in certain embodiments these ridges may aid in accurate dispension or allow the syringe to derive additional functionality, such as performing as a vacuum source. Ridges can be protrusions such as tabs, bubbles or continuous rings for single or repeated use or these ridges may be formed as indentations. Ridges may be formed in patterns, in various sizes and shapes or these ridges may be mixed and matched as required or desired. Ridges may also be formed from a soluble material and the resistive change may itself provide indication that the material has been substantially dissolved and dispensed. In some embodiments these ridges are formed primarily within the barrel portion of the syringe. In other embodiments these ridges may be formed on the plunger stem of the syringe. Ridges may be constructed to provide one type of resistive change during the aspiration stroke and a different resistive change to motion in the opposite direction.

27 Claims, 4 Drawing Sheets

U.S. PATENT DOCUMENTS

| | | |
|---|---|---|
| 5,531,703 A | 7/1996 | Skwarek et al. |
| 5,540,660 A | 7/1996 | Jenson |
| 6,171,285 B1 | 1/2001 | Johnson |
| 6,287,282 B1 | 9/2001 | Bonaldo |
| 6,368,305 B1 | 4/2002 | Dutton |
| 6,379,328 B1 | 4/2002 | Mac Clay |
| 6,419,656 B1 | 7/2002 | Vetter et al. |

FOREIGN PATENT DOCUMENTS

| | | |
|---|---|---|
| FR | 2 613 628 | 10/1988 |
| WO | WO89/09073 | 10/1989 |
| WO | WO99/55402 | 11/1999 |

* cited by examiner

SYRINGE DEVICE WITH RESISTIVE RIDGES AND METHODS OF USE

BACKGROUND OF THE INVENTION

The present invention relates generally to a hypodermic syringe and more particularly to a syringe device having at least one ridge within the barrel portion of the syringe or along the plunger stem of the syringe device.

Syringe devices may be designed or intended for single or repeated use and may be operated manually or all or a portion of their operation may be mechanized. In general, a syringe device is comprised of three basic components: a barrel, which is typically cylindrical, a plunger, and a gasket which is affixed to the plunger so as to move in conjunction with the plunger. The gasket is typically designed to substantially seal within the barrel such that during operation the units function as a displacement piston. As such, this piston configuration provides for two directions of axial movement which may generally be termed an aspiration cycle and a dispensing cycle. Needles, filters, drive mechanism, locks, and protectors, as well as other components, are often used to augment the basic syringe device. Commonly, the barrel portion is translucent to allow visualization of the contents such as medicinal fluids, body aspirates or glue. Accordingly, aspiration draws matter, such as fluids, into the syringe, or the negative pressure developed by the aspiration stroke may be used for other purposes, for example, to suction and hold parts being manipulated on an assembly line. Similarly, the opposite stroke provides an outward force that may be used, for example, to inject fluids, or to provide a puff of air to blow dust off of optics. Combining piston movements with valves allows syringe devices to function in other ways, such as a pump. Precise movements and operation can be accomplished in a number of ways, for example by driving the syringe plunger with a computer-controlled stepper motor. Due to low cost, ease of manufacture, and established use, when appropriate, syringe devices can be further innovated to provide novel functionality.

U.S. Pat. No. 2,549,417 to Brown entitled "Syringe ampoule" discusses temporary compartments for use within a hypodermic syringe. Accordingly, to provide for temporary compartments, by-pass ribs (the length of the by-pass ribs being greater than the width of the stopper) are projected into the barrel of the syringe. In such a manner, a valve of sorts is created by projecting ribs to establish communication between potentially a plurality of compartments. One use described provides for dry chemicals in one compartment that may be measured and transported in the device. Subsequently, providing a fluid passage (using the ribs as a valve) allows these chemicals to be mixed with a diluent and dispensed.

U.S. Pat. No. 2,591,046 to Brown entitled "Hypodermic syringe assembly" further discusses syringe configurations and among other things, provides for multiple ribs so that the liquid vehicle may pass through these passages.

U.S. Pat. No. 5,000,735 to Whelan entitled "Single use syringe" discusses general use of syringes and more particularly a means of preventing reuse, for example, by breaking off or otherwise separating the plunger or plunger gasket after downward movement.

U.S. Pat. No. 4,469,482 to Lissenburg entitled "Disposable hypodermic syringe" discusses various aspects of syringes, their composition and use.

U.S. Pat. No. 6,379,328 to Mac Clay entitled "Disposable syringe" discloses a novel piston design used generally for dispensing fluids, such as drugs.

U.S. Pat. No. 5,389,070 to Morell entitled "Syringe apparatus with a fluid reservoir for injecting and aspiration of fluids" discusses advantages of connecting more than one syringe via a three-way stopcock, for example.

Among other things, U.S. Pat. No. 6,171,285 to Johnson entitled "Retractable syringe" discusses plunger locks and needle retraction into the syringe barrel.

Another form of plunger lock or plunger inhibitor is discussed in U.S. Pat. No. 6,368,305 to Dutton entitled "Syringe plunger immobilizing device".

U.S. Pat. No. 5,480,064 to Yan entitled "Dispensing syringe for a fluid glue" discusses additional aspect of operating a syringe for dispensing fluids.

U.S. Pat. No. 4,430,079 to Thill entitled "Fluid dispensing device" among other things discusses coupling a syringe with a hose and providing for the application of a uniform force to the plunger to prove steady flow over a period of time.

For some applications it is useful to know the position of the plunger, as in a belt-driven infusion pump as discussed in U.S. Pat. No. 5,259,732 to Stern entitled "Syringe pump with syringe barrel position detector". Stern also discusses use of a pressure detector to detect occlusions. Other aspects of syringe use in infusion pumps may be found in U.S. Pat. No. 5,295,966 to Stern. Various aspects of driving syringes is also discussed within.

U.S. Pat. No. 6,287,282 to Bonaldo entitled "Syringe safety sleeve and adaptor" discusses attachment of a protective sleeve. Other attachments within or external to syringes, such as filters are discussed in U.S. Pat. No. 4,137,917 to Cohen entitled "Syringe filter unit".

U.S. Pat. No. 6,419,656 to Vetter entitled "Medical syringe with braked step-advance plunger" discusses plunger projections as well as a bypass passage forward of the piston. In certain positions the configuration may act with the by-pass groove and operation allows stop bumps to engage an elastically deformable brake element. At least two axially space projecting stop bumps are provided for on the stem or plunger rod. Vetter provides for a bypass passage forward of the plunger which may for example, hold a soluble medicament, but provides no mechanism to ensure that such a medicament is substantially dissolved and dispensed. The present invention discusses internal ridges formed from soluble components such as medicaments and provides a means in the form of resistive changes to assess when any such components have been substantially dispensed. In addition, Vetter discusses pairs of stop bumps on the plunger stem that act as brake elements to prevent the plunger from advancing too rapidly requiring that the user twist the piston to align for further advance. In some embodiments, the present invention seeks to simplify syringe operation providing the user with feedback regarding syringe speed or plunger position, such tactile feedback allowing operation of the syringe in stressful, poor lighting or other unfavorable conditions. Accordingly, Vetter does not contemplate rings or single bumps formed on the syringe stem so as to provide tactile feedback and does not suffer as a consequence. While the present invention primarily discusses ridges formed on the inner barrel of a syringe, some of this novel functionality may be derived by forming ridge structures on the plunger stem.

Accordingly, because of their simplicity, ease of manufacturing, low cost, varied materials, availability, adaptability and other aspects, it would be advantageous to further exploit the use of syringes. The present invention provides for a novel syringe device which provides a ridge in the form of a partial or tactile stop within the barrel of a syringe. Such innovation provides for new functionality and uses as will be further discussed herein.

SUMMARY

The present invention is a syringe in which one or more ridges are formed within the barrel of the syringe or along the plunger stem of the syringe device to provide tactile or sensory feedback in the form of resistive changes. The tactile feedback is useful to humans who are, for example, visually impaired, rushed, or in low lighting situations. The sensory feedback is also useful to machinery in automated operations.

"Ridge" as used herein means a protrusion or indentation formed within the barrel of a syringe or along the plunger stem of a syringe device. A ridge as used herein may be of desired size, shape, dimension, elasticity, and number so as to provide tactile or sensory feedback, typically in the form of a resistive change to axial movement of the gasket within the barrel. Tactile feedback may be sensed by a user or via a machine interface and provide indication of gasket position and/or speed and/or displacement, for example. Accordingly, a ridge may be substantially tactile, provide strong resistance to provide a stopping or holding action, provide substantially the same or different amounts of resistance depending on the direction of axial movement, be designed for one time use, be formed in a pattern to provide additional indication of position or speed, or otherwise be exploited to advantage.

DETAILED DESCRIPTION OF THE PREFERRED EMBODIMENTS

Figure 1:
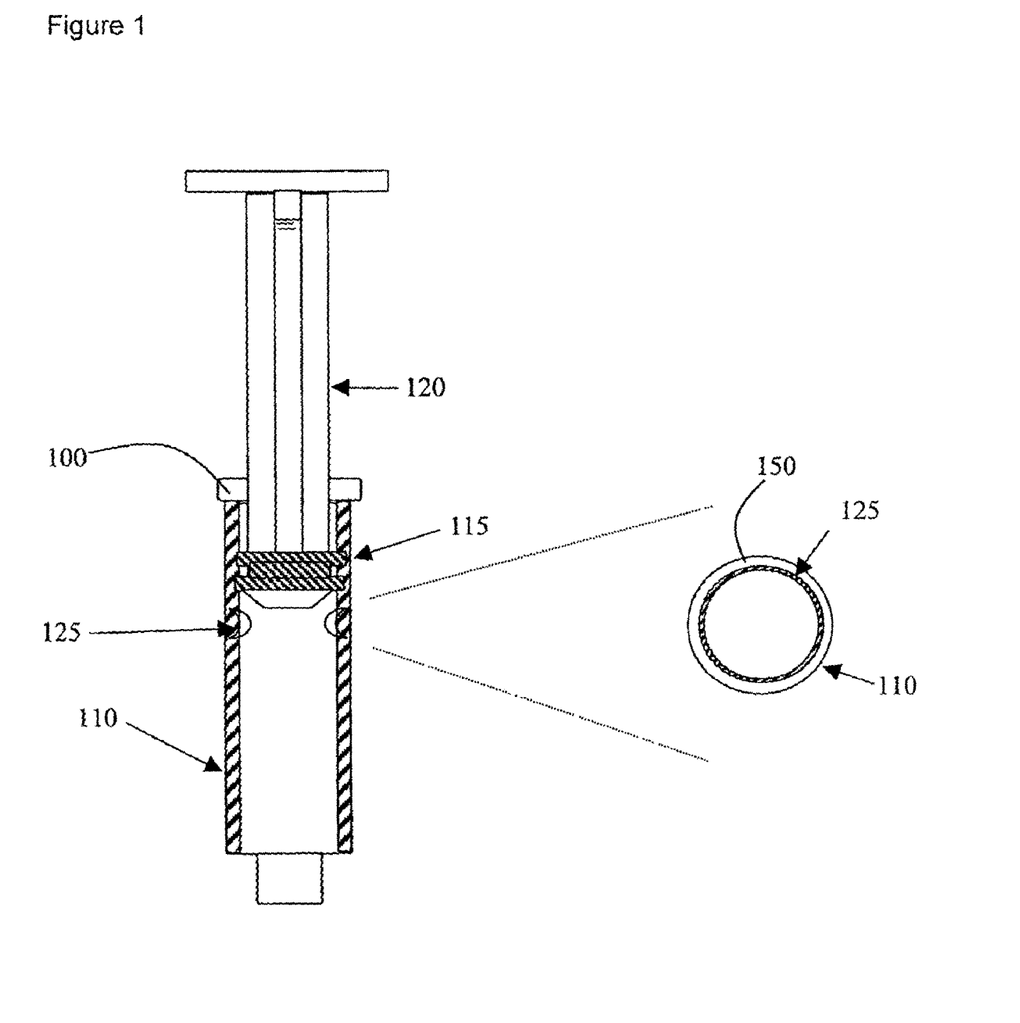
FIG. 1 shows a syringe device of the present operation with novel tactile ridge.

FIG. 1 shows syringe device 100 of the present invention having a cylindrical tube or barrel 110 with plunger 120 and ribbed gasket 115 attached to the plunger 120. A novel, tactile ridge 125 has been implemented within the barrel 110. (Please note that the ridge 125 is illustrated in FIG. 1, as are all of the ridges illustrated in subsequent figures, in exaggerated size for clarity. The actual size and shape of a particular ridge depends on the use of the device.) The tactile ridge 125 is further shown in expanded cross-section as a protruding ring within the barrel 110. The tactile ridge 125 is implemented so as to provide a slight, incremental resistance that may be physically sensed as the gasket 110 is caused to move over the tactile ridge. As shown in expanded view in FIG. 1, the tactile ridge 125 in this instance is formed as an internal ring. As will be described further, protrusions such as bumps or indentations formed within the syringe barrel may also be used to provide such a tactile feedback.

For many applications such tactile ridges are preferably implemented in a manner that does not break the seal within the syringe to a degree that undermines or otherwise impedes intended use. The tactile ridge 125 provides feedback that may be useful to human users or may be sensed in various ways when machine interfaced thus providing information regarding position or movement of the syringe plunger. In the illustrated embodiments, the tactile ridge 125 (225 and 331 through 335 in subsequent drawings) is a rounded protrusion or nub projecting axially from the interior wall of the barrel 210. But any shape, such as square, rectangular, wedged, polygonal, etc., can be used, depending on the materials used, the manufacturing process, and the degree of tactile feedback desired.

Figure 2A:
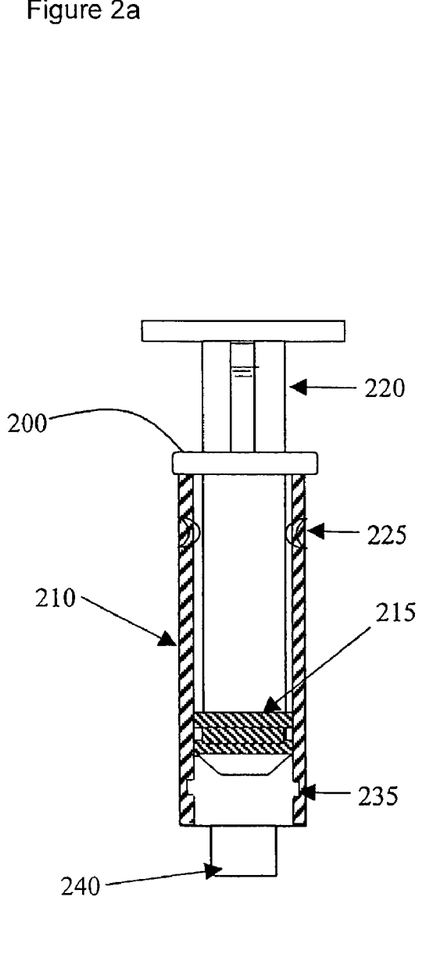
FIG. 2a shows a syringe device of the present operation with novel impeding ridge with plunger gasket in a forward position (prior to aspiration stroke).

The use of tactile feedback is advantageous in a variety of circumstances, for example, it may facilitate usage of a syringe for the visually impaired. Accordingly a series or coded (patterned) series of such tactile ridges could extend such functionality. Accordingly the present invention may be used to provide tactile feedback at volume intervals, such as each 1 cc, may be used in conditions 160 with restricted lighting, or may be used under conditions when it may be advantageous to free some attention, for example, during emergency medical situations encountered by the military or in trauma centers. Tactile ridges may be incorporated to work in conjunction with various syringes innovations such as compartments as previously described FIG. 2a shows a syringe device 200 of the present invention having a cylindrical tube or barrel 210 with ribbed gasket 215 attached to plunger rod 220. A more substantial tactile ridge in the form of an impeding ridge 225 has been implemented as a temporary impediment to movement. As diagramed, the impeding ridge 225 provides sufficient resistance so as to keep the plunger 220 from returning past the impeding ridge 225 when the open end 240 of the syringe is substantially occluded during the aspiration stoke (plunger retraction). As the plunger 220 is retracted with the inlet occluded, a negative pressure (vacuum) is developed. Such vacuum may be exploited in a variety of ways, which will be further discussed in association with FIG. 2b.

Figure 2B:
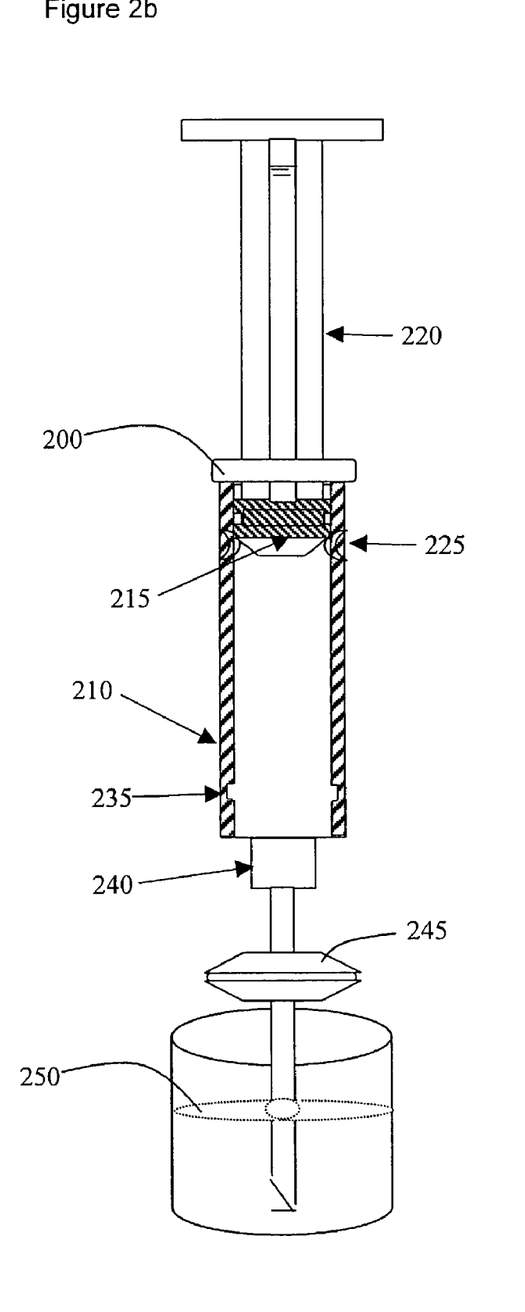
FIG. 2b shows a syringe device of the present invention with novel impeding ridge in retracted position (subsequent to an aspiration stroke).

FIG. 2b shows a syringe device 200 having a cylindrical tube 205 with ribbed gasket 215 attached to the interior end plunger 220. A novel tactile ridge, in the form of an impeding ridge 225 has been implemented in the barrel of the syringe as described in association with figure 2a, so as to provide sufficient resistant to keep the plunger from returning to its forward position of FIG. 2a, during intended use. In this instance, to better describe use of the syringe 200 as a vacuum device, the syringe tip 240 is shown attached to a filter apparatus 245. The filter apparatus 245 is submerged in a vessel containing a particle suspension 250. When submerged, the plunger is retracted from its forward position of FIG. 2a, which is accomplished by retracting the syringe plunger, thereby forcibly drawing the gasket 215 over to the top side of the impeding ridge 225. Such movement initiates the aspiration of particle suspension and will continue, typically until the vacuum is depleted or other factors affect the system. Material captured by the filter apparatus could be examined microscopically, for example. Other advantages of such a configuration are discussed in co-pending United States patent application entitled Method of Depositing Material and Density Gradients of Material from Sample Suspensions and Filter Devices for Same, filed on Aug. 26, 2002, application number 10/228,353.

As an example of another configuration ridge for tactile feedback, an indentation 235 is shown in the barrel 210 in FIGS. 2a and 2b. This indentation 235 is preferably of less width than the width of the gasket 215, or the gasket 215 is selected of material of sufficient elasticity, in order to prevent leakage around the gasket 215. As the plunger 220 moves the gasket 215 axially within the barrel 210, the user will feel different sensations as the gasket 215 moves over a protruding ridge 225 than when the gasket 215 moves over an indentation 235. The indentation 235 therefore provides the user with more detailed feedback as to the location of the plunger 220 within the barrel 210. As discussed above with respect to different shapes of the protruding ridge 225, this difference is sensation may be exploited for different applications.

Figure 3:
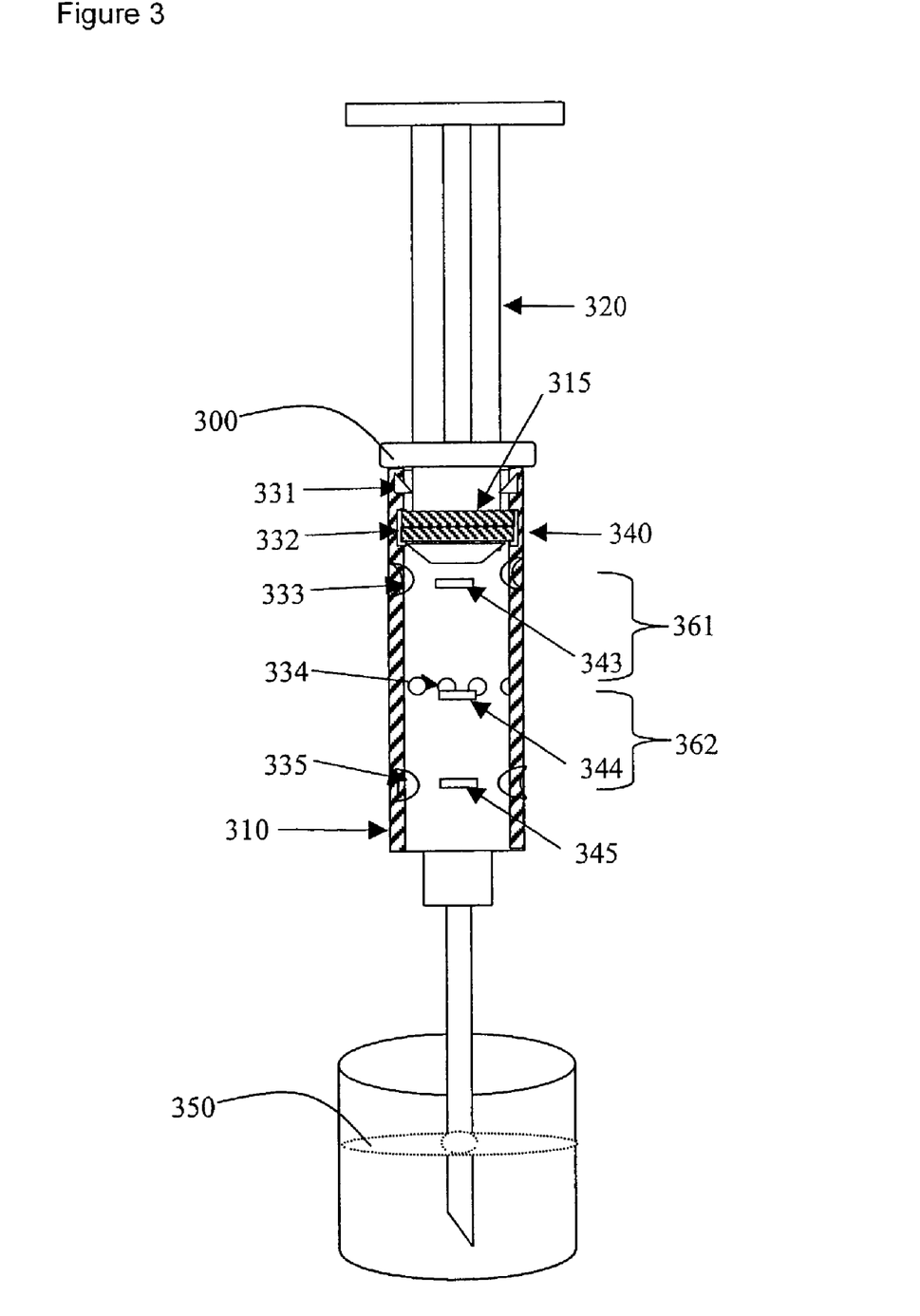
FIG. 3 shows a syringe device of the present invention in retracted position with two impeding ridges in the syringe barrel.

FIG. 3 shows another configuration and use of syringe device 300 of the present invention. As diagramed the syringe device has five ridges identified as 331, 332, 333, 334, and 335. The uppermost ridge 331 has been designed as a wedge to facilitate assembly of the syringe device (insertion of the plunger gasket assembly into the barrel 310) and inhibit separation of these components. For some applications, or to prevent spillage, for example, it may be desirable to provide such an impeding ridge 331 in the vicinity of the upper barrel of the syringe 300. Typically such impediment should be implemented so as not to inadvertently dislodge the gasket if disassembly is required or desired.

Beginning with the plunger 320 down (not shown) and the tip portion of the syringe 300 submerged in fluid 350 as shown, fluid 350 may be aspirated into the syringe 300 by retracting the plunger 320, drawing attached gasket 315 to ridge 332, a position in this instance intended to aspirate slightly more fluid 350 than is required for use, in the form of a priming volume to purge trapped air, for example. Typically, the syringe 300 is then inverted to facilitate priming which is accomplished by advancing the plunger 320 from ridge 332, to, in this instance, tactile ridge 333. Then the plunger 320 may be further advanced from tactile ridge 333 to another, in this instance tactile ridge 334. As illustrated, the ridges are formed on the interior wall of the barrel 310 as a series of round shaped protrusions or nubs, but can be of a different shape or size, or even of varying shapes and sizes, in order to provide more detailed tactile feedback. As described, this movement displaces the fluid volume 361 that exists between the two ridge positions 333 and 334. To provide additional indication of position or volume, accompanying markings striations 341 and 342 have been formed externally on barrel 310. In such a manner, the syringe device 300 provides a means to dispense preset fluid volumes with ease, and relative accuracy while providing indication of the position of the gasket 315 during operation.

Advancement of the plunger 320 may continue from ridge 334 (for example after waiting ten seconds) as required or desired, to tactile ridge 335, therefore in this instance providing a level of control over the dispensing of two fluid volumes, over a desired time interval.

The dimensions and sizes of the ridges 331 through 335 and the materials of the syringe barrel 310 should be considered for use. For example, gaskets with relatively elastic properties (e.g. rubber like compounds) will understandably perform different than firmer Teflon coated plastics or other materials. A small striation, scribe or bump encountered by a Teflon gasket may provide sufficient tactile feedback whereas a more substantial ridge may be required to achieve the same ends, employing a more elastic material.

As describe, ridges of various types may be formed or distributed over an effective area to provide sufficient tactile resistance. Rounded contact surfaces, to minimize abrasion to the gasket 315 are preferable but not required by the scope and intent of the present invention. Similarly, extended ridges in the form of narrowings or widenings of the syringe body are also considered within the scope of intended functionality of the present invention.

Figure 4A:
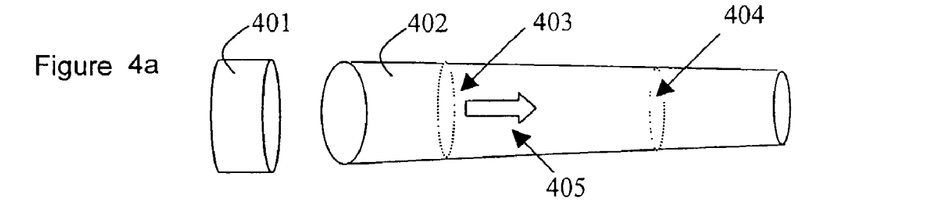
FIG. 4 shows a variety of ridge configurations.

FIG. 4a shows an alternative embodiment. In this embodiment, the ridge is formed by a tapering of the barrel of the syringe, along some portion or even substantially all of the syringe barrel. When the sealing gasket 401, with appropriate elastic properties, is inserted into the hollow cylindrical syringe barrel 402 and moved from approximate position 403, in the direction of the arrow 405, towards approximate position 404, an increase in resistance is generated due to frictional forces. This increase may be sensed, by a human user or machine-sensors interfaced to the plunger (not shown) and exploited to provide information as to the position of the sealing gasket 401 within the barrel 402. The syringe device is so formed and materials selected so that the seal between the sealing gasket 401 and the barrel 402 is substantially maintained during operation. If required or desired, however, the resistance, for example in approximate area 404, could be substantial enough to act as a mechanical stop, for intended use.

Figure 4B:
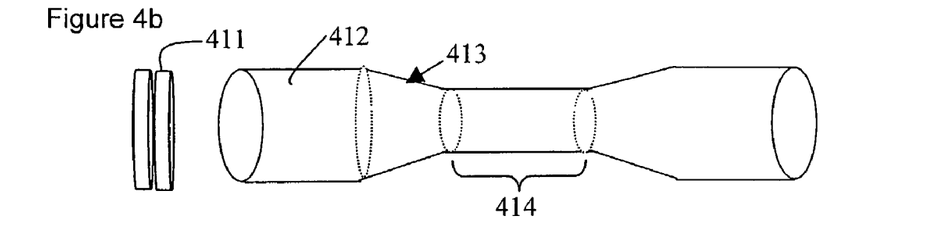

FIG. 4b shows a embodiment in which different resistances are generated in different sections of the barrel of the syringe. In this embodiment, sealing gasket 411 is advanced, typically by pushing or pull it via the attached plunger (not shown), through approximate regions 412, 413, and 414. During passage through region 412, the sealing gasket 411 encounters constant resistance. During passage through region 413, an increase in resistance is generated, and sensed. The resistance then remain relatively constant over some other a region of the syringe barrel, such as that designated as 414. Various forms of tapering may be implemented as required or desired to provide feedback to the human user or machine-interfaced sensors.

Figure 4C:
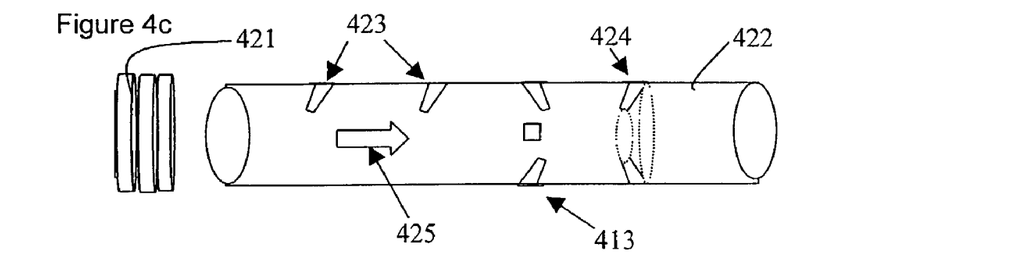

FIG. 4c shows other embodiments of ridges in the form of deformable tabs projecting into the interior wall of the syringe barrel 422. Ridges 423 are designed and intended in this instance to provide a certain resistance to movement as the sealing gasket 421 is pushed over them in the direction of movement indicated by arrow 425. Similarly, when the sealing gasket 421 is moved over these ridges 423 in the opposite direction, the design and implementation provides slightly less resistance than was generated in direction 425. Further along syringe barrel 422, ridges 413 have been implemented as distributed tabs around the interior of the barrel 422, providing a resistance increase that is lower in direction 425 and higher in the opposite direction. Alternatively, these ridges may take the form of a ring 424, projecting circumferentially around the interior of the barrel 422, instead of as tabs.

Figure 4D:
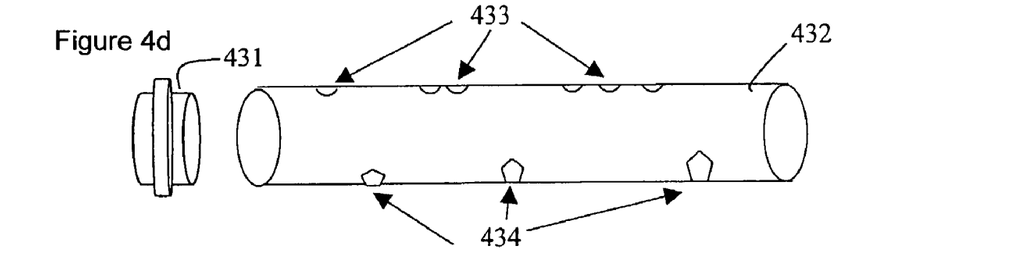

FIG. 4d shows sealing gasket 431 for insertion into syringe barrel 432 having ridges 433 formed on the interior wall of barrel 432 in the form of coded bumps. The number and interval of resistive pulses generated and sensed as the sealing gasket 431 is advanced over them, provides information such as position, movement, speed, or displaced volume. Such information may be useful as sensed by the visually impaired, in poor lighting conditions, etc. Also, machine-interfaced sensors could employ this information to advantage, for example, to simplify position detection or otherwise provide feedback for robotic operation. Alternatively, for the same stroke distance, using larger syringe barrels may simplify the mechanics or electronics necessary to accomplish a desired task. Similarly, in certain situations, such as isolating electronics from fluids may favor such implementation. An alternate series of ridges in the form of nubs 434 are designed to provide information in the form of resistive pulses that change in magnitude as gasket 431 is caused to pass over them. Both ridges 433 and numbs 434 can project as tabs from the interior of the barrel 432 or as circumferential rings projecting from the interior of the barrel 432, as described above with respect to FIG. 4c. The number, size, position, sequence, and resistance of the ridges 433 or numbs 433 can be designed as needed to provide feedback to the human user or the machine-interfaced sensor.

Figure 4E:
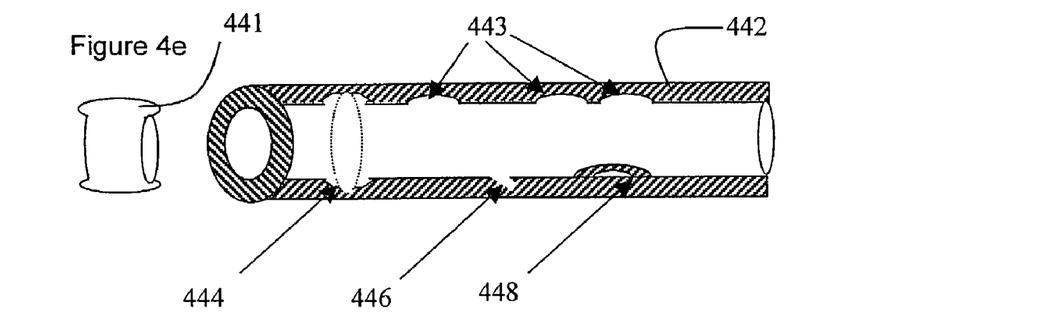

FIG. 4e shows additional embodiments with ridges of various types formed as indentations 443, 444 in the interior wall of the syringe barrel 442 so as to provide resistive changes as the sealing gasket 441 passes over them, is delayed by them, or its motion is substantially halted, as desired or required. The sealing gasket 441 has been designed and in this instance customized to operate in this barrel 442. Additionally, ridge 448 has been formed as a protruding ridge in the form of a collapsible bubble, designed to be sensed once, thereafter providing no further resistive change, if subsequently encountered. Alternatively, such a single sense element 446 could be reversed in curvature and sprung into an adjacent indentation, or alternatively a single sense element could be a break-off or otherwise separating component, as required or desired.

Another useful form of ridge could be provided by chemicals formed, for example, as rings within the barrel 442. In this instance the ridge resistance may provide information regarding mixing, quantity of dissolved chemical dispensed, etc.

While preferred embodiments of the present invention are shown and described, it is envisioned that those skilled in the art may devise various modifications of the present invention without departing from the spirit and scope of the appended claims.

I claim:

1. A syringe device comprising:
   a hollow member having an inner wall,
   a sealing gasket disposed within said member,
   a plunger connected to said scaling gasket, said plunger implemented to produce movement of said sealing gasket within said member along a path defined by a first position and a second position, in a first direction and in a second direction,
   at least one ridge formed on said inner wall between said first position and said second position, each said at least one ridge providing a change in resistance to said movement of said sealing gasket along said path and said sealing gasket being configured to maintain a seal between said sealing gasket and said inner wall during said movement.

2. The device of claim 1, wherein said at least one ridge comprises at least one tab.

3. The device of claim 1, wherein said at least one ridge comprises a continuous ring.

4. The device of claim 1, wherein said at least one ridge comprises a collapsible bubble.

5. The device of claim 1 wherein said change provided by at least one of said at least one ridge is an increase.

6. The device of claim 1 wherein said change provided by at least one of said at least one ridge is a decrease.

7. The device of claim 1 wherein said at least one ridge is made of a material that dissolves when a solvent is aspirated.

8. The device of claim 7, wherein said change in resistance provides an indication of a continued presence of a material, not yet dissolved in said solvent.

9. The device of claim 1 wherein said at least one ridge comprises a plurality of ridges.

10. The device of claim 9, wherein said plurality of ridges are arranged in a sequence.

11. The device of claim 9, wherein said plurality of ridges comprises ridges of at least two different sizes, wherein said change in resistance depends on the size of said ridge.

12. The syringe device of claim 1 wherein said at least one ridge provides a first change in said resistance to said movement in said first direction and a second change in said resistance to said movement in said second direction.

13. The device of claim 12, wherein said at least one ridge comprises at least one tab.

14. The device of claim 12, wherein said at least one ridge comprises a continuous ring.

15. The device of claim 12, wherein said at least one ridge comprises a collapsible bubble.

16. The device of claim 12, wherein said change provided by at least one of said at least one ridge is an increase.

17. The device of claim 12, wherein said chance provided by at least one of said at least one ridge is a decrease.

18. The device of claim 12, wherein said at least one ridge is made of a material that dissolves when said gasket moves over said ridge.

19. The device of claim 12, wherein said at least one ridge comprises a plurality of ridges.

20. The device of claim 19, wherein said plurality of ridges are arranged in a sequence.

21. The device of claim 19, wherein said plurality of ridges comprises ridges of at least two different sizes, wherein said change in resistance depends on the size of said ridge.

22. A syringe device comprising:
   a member defining a passageway through said member, said passageway having a first region and a second region, said first region having an inner diameter tapering from a first inner diameter at a first end distal to said second region to a second inner diameter at a second end proximal to said second region;
   said second region having said second inner diameter throughout;
   a sealing gasket disposed within said cylindrical member; and
   a plunger to cause a movement of said gasket within said passageway in a first direction and in a second direction;
   said gasket maintaining a seal between said gasket and said passageway during said movement; and
   a resistance to said movement is constant in said second region and is variable in said first region.

23. The syringe device of claim 22, wherein said second inner diameter is smaller than said first inner diameter.

24. The syringe device of claim 23, further comprising a third region proximal to said first region and having said first inner diameter throughout and wherein said resistance is constant in said third region.

25. The syringe device of claim 22, further comprising a third region proximal to said first region and having said first inner diameter throughout and wherein said resistance is constant in said third region.

26. The device of claim 9, wherein said plurality of ridges comprises ridges of at least two different shapes, wherein said change in resistance depends on the shape of said ridge.

27. The device of claim 19, wherein said plurality of ridges comprises ridges of at least two different shapes, wherein said change in resistance depends on the shape of said ridge.

* * * * *